United States Patent [19]

Minin et al.

[11] Patent Number: 5,543,410
[45] Date of Patent: Aug. 6, 1996

[54] PHARMACOLOGICAL USE OF PHTHALOYLHYDRAZIDE DERIVATIVES; COMBINATION AND APPLICATION THEREOF

[75] Inventors: Leonid Minin; Slava Saizev, both of Geneve, Switzerland

[73] Assignee: L.I.M.A.D. Limited, Douglas, Isle of Man

[21] Appl. No.: 551,886

[22] Filed: Oct. 23, 1995

Related U.S. Application Data

[63] Continuation of Ser. No. 198,888, Feb. 18, 1994, abandoned.

[30] Foreign Application Priority Data

Feb. 19, 1993 [CH] Switzerland ................. 530/93

[51] Int. Cl.$^6$ ..................................................... A61K 31/50
[52] U.S. Cl. ............................................................... 514/248
[58] Field of Search ................................................. 514/248

[56] References Cited

U.S. PATENT DOCUMENTS

| | | | |
|---|---|---|---|
| 2,453,578 | 11/1948 | Lacey et al. | 544/237 |
| 3,753,988 | 8/1973 | Rodway et al. | 544/237 |
| 3,864,343 | 2/1975 | Inoue et al. | 544/237 |
| 3,957,776 | 5/1976 | Podesua et al. | 544/237 |
| 4,011,219 | 3/1977 | Nishii et al. | 544/237 |
| 4,226,993 | 10/1980 | Buckler et al. | 544/237 |
| 4,250,180 | 2/1981 | Kane et al. | 544/237 |
| 4,334,069 | 6/1982 | Buckler et al. | 544/237 |
| 4,355,165 | 10/1982 | Boguslaski et al. | 544/237 |
| 4,393,062 | 7/1983 | Brittain et al. | 544/237 |
| 4,440,763 | 4/1984 | Loven | 424/230 |
| 4,665,181 | 5/1987 | Thomas et al. | 544/237 |
| 5,391,555 | 2/1995 | Marshall et al. | 514/311 |

FOREIGN PATENT DOCUMENTS 1100911 1/1968 United Kingdom.

OTHER PUBLICATIONS

Merck Index, Ninth Edition pp. 5420, 1976.

Primary Examiner—José G. Dees
Assistant Examiner—Deborah Lambkin
Attorney, Agent, or Firm—Notaro & Michalos

[57] ABSTRACT

The invention pertains to use of phthaloylhydrazide derivatives and salts thereof as anti-inflammatory and antitoxic agents in human and veterinary medicine, and it pertains in particular to use of 5-aminophthaloylhydrazide and of the sodium salt thereof.

10 Claims, No Drawings

PHARMACOLOGICAL USE OF PHTHALOYLHYDRAZIDE DERIVATIVES; COMBINATION AND APPLICATION THEREOF

This application is a continuation of application Ser. No. 08/198,888, filed Feb. 18, 1994 abandoned.

FIELD AND BACKGROUND OF THE INVENTION

The present invention pertains to indications of the pharmacological effectiveness of a significant group of compounds consisting of phthaloylhydrazide derivatives with the following general formula:

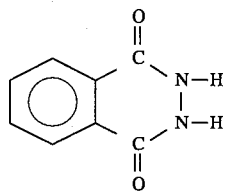

SUMMARY OF THE INVENTION

Certain derivatives of 5-aminophthaloyl hydrazide have been used as chemical reagents in biochemical analysis. Practical applications for certain other derivatives, namely 2,3-dihydrophthalazine-1,4-dione, the sodium salt of 4-amino-2,3-dihydrophthalazine-1,2-dione, the sodium salt of 5-amino-2,3-dihydrophthalazine-1,2-dione, 4,5-diamino-2,3-dihydrophthalazine-1,2-dione have not been identified, nor have salts of the previously indicated compounds been used.

Attempts to use 2,3-dihydrophthalazine-1,4-dione and certain derivatives for reducing serum cholesterol levels (J. H. Hall et al., "Effect of 2,3-dihydrophthalazine-1,4-dione on Sprague-Dawley Rats' Lipid Metabolism and Serum Lipoproteins," *Biomed. Biochem. Acta* V, 47 (4–5), pp. 423–433, 1988) by modifying levels of lipids with extremely low densities have occurred. It was determined, however, that this particular compound was relatively toxic when it was administered in doses of 20 mg/kg, although it did display an extremely high level of activity. Nevertheless, the anti-inflammatory and anticancer effects of derivatives belonging to this group of compounds have not been recognized and have not been described within medical literature.

For the first time, it has been possible to demonstrate phthaloylhydrazides' original and unique mode of action which, instead of emerging from analysis of their chemical properties, only became evident from in vivo administration of these compounds.

Pharmacological testing of compounds belonging to the phthaloylhydrazide group and salts of these compounds allowed identification of 5-aminophthaloylhydrazide as the compound offering the most significant therapeutic effectiveness, and it is wholly non-toxic in situations where acceptable dosages are used.

The results of pharmacological and toxicological tests are provided subsequently.

DESCRIPTION OF THE PREFERRED EMBODIMENTS

Chemical Data:
(a) Physical Properties 5-aminophthaloylhydrazide is a pyridazine compound with a low molecular weight (less than 200). Its melting point is less than 250° C.

pH—solubility profile: pH of 6.5, c=2 mM pH of 7.4, c=12 mM

The octanol/water distribution coefficient is pH dependent.

pH of 7.4, c=0.2

(b) Chemical Properties pK=6.3

Stability: this compound is stable under anhydrous conditions (storage period>1 year). In some instances, however, it is unstable in aqueous solutions (probably on account of cooxidation with certain mixtures of substances which are present in trace quantities. Expiration period for aqueous solution>ten to twenty hours.

Active rotation: absent.

Toxicological Data (a) Acute Toxicity

Acute toxicity tests were performed upon two species (mice, rats). More than 80 mice and more than 100 rats were used. The drug was administered orally and parenterally in doses of 500 mg/kg to 2,500 mg/kg (individual doses). The observation period was fourteen days. Morphological alteration of hepatic, renal, cardiac, and cerebral tissue was not observed. Percentages of lethal outcomes within the test groups did not exceed the percentage for the control group.

(b) Mutagenicity

Mutagenicity was measured by means of Ames' bacterial testing method. Tests were performed with TA 100, TA 102, and TA 97 *S. typhi* strains. The microsome activator method using rats' livers where induction had occurred with methylcolanthrene was adopted. The respective data indicated that 5-aminophthaloylhydrazide did not possess inhibitory or mutagenic activity at levels between 0.01 mg/ml and 2 mg/ml.

(c) Toxicity in terms of Reproduction

Tests pertaining to teratogenicity and embryotoxicity were performed upon fifty-eight pregnant female rats. A single dose (60 mg/kg) was injected intraperitoneally on the first, third, seventh, tenth, fourteenth, or seventeenth days of gestation. These rats were decapitated on the twenty-first day of gestation, and uteri and fetuses were examined. No fetal abnormalities were found. Uterine attachment locations, numbers, weights, and fetal mortality levels did not differ from data obtained for the control group.

(d) Cytotoxicity

The cells which were targeted were lymphocytes, macrophages, and fibroblasts. Survival after twenty-four hours of in vitro exposure to 5-aminophthaloylhydrazide in concentrations of 0.01 mmol/liter to 0.8 mmol/liter was determined by means of protein incorporation and/or synthesis. No toxicity was observed for all of the dosage levels being tested.

The allergenic activity of this drug was examined with guinea pigs, and no indications of allergies were observed for subcutaneous or oral administration. Erythema was not encountered at the site of administration, even in the instance of large doses. Properties causing local irritation were not observed in situations where 20 mg to 100 mg doses had been administered.

Research concerning Influence upon the Central Nervous System

Doses of 30 mg/kg and 60 mg/kg according to body weight were used for studying pharmacological properties in relation to the central nervous system. Selection of this dosage level was based upon criteria in terms of safety in using drugs.

Neuropharmacological effects were studied in sexually mature male mice from unspecified strains. A solution of the drug was administered intraabdominally to these mice, with weights of 18.0 g to 20.0 g, and neuropharmacological effects were studied in terms of changes in the natural orientation reflex, in induced aggressiveness, and in muscle tone. Changes in natural orientation were recorded according to current methods. For determining the drug's influence upon induced aggressiveness, the electrical stimulation method (an electrical current which caused pain was transmitted) was adopted.

Changes in muscle tone were measured according to the "pivot pin" method.

In doses of 30 mg/kg and 60 mg/kg according to body weight, this drug did not suppress the natural orientation reflex, did not cause changes in muscle tone, and did not alter the threshold for sensitivity to pain.

The influence of this particular drug upon the duration of general anesthesia induced by Hexenalum was also studied. In this instance, it was administered in 30 mg/kg and 60 mg/kg doses, fifteen minutes prior to administration of a Hexenalum solution in 80 mg/kg doses. With the doses which were being used, 5-aminophthaloylhydrazide did not produce a noteworthy prolongation of unconsciousness induced by Hexenalum.

When the anticonvulsive activity of the compound was investigated, it was determined that prior administration to mice in doses of 30 mg/kg and 60 mg/kg according to weight did not prevent convulsions caused by Corazolum and strychnine, which had been induced with intravenous titration of convulsive drugs. The convulsions which occurred were not reduced by the previously cited doses of 5-aminophthaloylhydrazide.

Research concerning the Effects of the Sodium Salt of 5-aminophthaloylhydrazide upon the Cardiovascular System The influence of the sodium salt of 5-aminophthaloylhydrazide upon blood pressure was studied in male rats weighing from 230.0 g to 270.0 g, in a controlled experiment where the rats were anesthetized with urethane. Blood pressure levels were tape-recorded, by means of an electrical kymograph.

At the same time, electrocardiograms for the second standard position were recorded, along with frequency and depth of breathing by means of a Morey capsule. 5-aminophthaloylhydrazide was administered through the femoral vein, in the form of an aqueous solution which prepared within a 2 percent sodium bicarbonate solution (pH=8.2), in doses of 30 mg/kg, 60 mg/kg, and 50 mg/kg according to weight. Research concerning 5-aminophthaloylhydrazide was performed upon sixteen rats.

Results: Intravenous administration of a 1 percent 5-aminophthaloylhydrazide solution at a rate of 0.6 ml per minute was followed by a brief rise in blood pressure, according to an average of $1.57 \pm 5.93$ percent in relation to the initial level. Sudden upward fluctuations in blood pressure were not observed during administration of 5-aminophthaloylhydrazide in 30 mg/kg doses, nor in 50 mg/kg kilogram doses. Five minutes after administration of 5-aminophthaloylhydrazide had commenced, blood pressure declined gradually, and, within an average of thirty minutes, it returned to the initial level.

Average fluctuations in blood pressure levels thirty minutes after administering 5-aminophthaloylhydrazide were $2.79 \pm 0.72$ in comparison with initial blood pressure levels.

Changes in electrocardiogram parameters for the heart were not observed during completion of the experiment, and no impairment of respiratory functions was observed in situations where 5-aminophthaloylhydrazide was administered in doses of 30 mg/kg and 60 mg/kg according to weight.

During experimental investigation of 5-aminophthaloylhydrazide administered in doses of 30 mg/kg and 60 mg/kg according to weight, no unfavorable influence upon the cardiovascular system or upon respiratory functions from this particular substance was encountered. It is possible to explain the tendency for blood pressure to rise shortly after intravenous administration as a (compensatory) response reaction by rats' cardiovascular systems to a change in the alkalinity of their blood. This factor was demonstrated by administration of a 2 percent sodium bicarbonate solution.

Varieties of Medications

The types of medications which are most widely used have been: vials for intravenous and intramuscular injections, suppositories for rectal administration, and solutions for gargling.

The sodium salt of 5-aminophthaloylhydrazide, with a level of purity which was at least 96 to 98 percent, was diluted in the smallest possible volume of specially deionized water, and it was placed in vials with opaque walls, so that each vial would contain 100 mg of the compound. Subsequently, the vials were lyophilized and they were sealed with sterile caps, which were secured thereafter. The vials were then sterilized by maintaining a temperature of 140° C. to 160° C. for sixty minutes.

The containers used for animals contained a larger quantity of the drug: 250 mg.

Aqueous solutions of this compound remain fully active for sixty to eighty minutes.

(2) The solution intended for gargling was prepared in a similar manner, although each portion contained 250 mg of the sodium salt of 5-aminophthaloylhydrazide. Dilution in a minimum quantity of water (=3 percent) took place prior to use.

(3) A combination of 5-aminophthaloylhydrazide and its sodium salt, which was intended for intramuscular injections for animals, was prepared by mechanical mixing of previously measured amounts of each substance defined by weight, with use of a milling unit. This mixture was diluted in water prior to use, and stirring was performed. Intramuscular administration of the suspension obtained in this manner took place thereafter.

(4) Suppositories intended for rectal administration were prepared with use of "Salo" ointment according to specific techniques which had been developed for this purpose. The respective quantities of the sodium salt of 5-aminophthaloylhydrazide varied from 50 mg (for children) to 100–200 mg in various samples.

All of the compounds within this group contain various chemical radicals where hydrogen atoms are substituted for the benzene ring and for the respective lateral groups. It has been demonstrated that these compounds possess anti-inflammatory, antitoxic, and anticancer properties.

It has been determined experimentally that 5-aminophthaloylhydrazide provides a higher level of pharmacological activity. These compounds in the form of salts, or combinations thereof, are principally recommended for use in medical and veterinary practice.

The therapeutic effects of the respective compound's action are attributable to the following properties:

I. Antioxidant action

Although the effectiveness of 5-aminophthaloylhydrazide is thirty to fifty times less than that of previously identified antioxidants within systems adopted as models (micellar phase), with use of unsaturated fatty acids and durable radicals, it was nevertheless possible for the retardation constant for peroxidation of blood plasma to increase ten to twelve times, only two to five minutes after administration. From the standpoint of effectiveness, this compound is therefore significantly superior to known antioxidants such as dibunol, alphatocopherol, and superoxydismutaze (SOD). This fact has been confirmed by analysis of peroxidation products. In models corresponding to acute purulent inflammation (wounds) caused by inoculation of a suspension of pathogenic microbes, such as *E. coli* and *S. aureus*, pentane production within air exhaled by the respective animals was measured. A reduction in pentane was already observable thirty to sixty minutes after a single administration of the drug, until a normal level was attained. This phenomenon offered definitive confirmation of the effectiveness of 5-aminophthaloylhydrazide as an antioxidant.

II. An increase in leucocyte adhesion properties and intensification of chemotaxis, thereby causing accumulation of neutrophils in the site of inflammation: this phenomenon was specifically demonstrated in a situation involving inflammation of the cornea.

III. In vivo (whole blood) intensification of the functional activity of neutrophils; an increase in the rate at which superoxide radicals formed (NST test); a 60 to 80 percent increase in phagocyte activity (LATTICE test).

IV. Modification of the macrophage metabolism, both in vitro and in vivo, with transformation of a certain portion of macrophages into killer cells which are capable of dissolving cancer cells affected by the SV-40 virus, or cells obtained from culturing of gliomas.

5-aminophthaloylhydrazide's observed property of easily passing through the hydrophobic phase of living membranes is of considerable significance, inasmuch as it ensures protection of healthy cells from excessive production of free radicals released by leucocytes, with these free radicals being intended for distribution of extraneous agents. Moreover, this compound does not assimilate membranes of microbial cells, and microbial cells are therefore easily exposed to the action of free radicals.

At the present time, similar drugs which simultaneously perform the two opposite actions, namely leucocyte activation and protection of healthy tissue from excessive activity on the part of leucocytes, have not yet been described.

Existing (analogous) drugs are intended to provide direct antibacterial action or to influence metabolic processes (steroid hormones).

Insofar as tumoral tissue may be concerned, derivatives of 5-aminophthaloylhydrazide offer a targeted mode of action.

1. The drug considerably increases fluidity of the lipid phase of tumor membranes (by 14 to 19 percent), and, at the same time, it does not influence the structure of intact cells (1 to 4 percent) in any particular manner.
2. This phenomenon intensifies the action of the tumor necrosis factor (TNF) in mutated cells while protecting undamaged cells (tissues) within the body at the same time.

Analysis of pharmacokinetic aspects has demonstrated that, in situations where 5-aminophthaloylhydrazide is intravenously administered, its half-life within blood plasma is from five to fifteen minutes.

The general renal clearance test provides 50 to 80 ml per minute as a result (in the instance of administration to rabbits, however, the result was 5 to 50 mg/kg). The length of the half-life of this particular compound increases to forty to sixty minutes for intramuscular and rectal administration, whereas it is four to five hours when a mixture is administered. In terms of the hydrophobic phase of living membranes, 5-aminophthaloylhydrazide remains active for several hours.

Metabolic products were also identified. More than 90 percent of the compound decomposes into 5-aminophthalic acid, oxygen, and nitrogen. Most of the aminophthalic acid is expelled from the body without undergoing modification. Using a combination of the readily soluble sodium salt of 5-aminophthaloylhydrazide and hydrophobic 5-aminophthaloylhydrazide in proportions of 1:1 and 1:0.5 prolongs the therapeutic effect. This factor is especially important in treating intestinal infections in livestock, where use of the drug must begin in a relatively rapid manner.

It is significant to observe that it is likewise possible to produce a buffer solution with a pH of 7.8 to 8.0 for parenteral administration. In some instances, chronic diseases and autoimmune diseases require different rates of administration of the drug. Nevertheless, there is a general rule for every situation, independently of the form and stage of a disease, whereby the initial rate of administration must be less frequent (every one to three days), with a subsequent increase to a frequency of once or twice daily. This rule is especially important in terms of treating non-specific ulcerative colitis, Crohn's disease, malignant tumors, diffuse sclerosis, certain complications arising from diabetes, specific cataracts, etc.

The antitoxic effects of this compound in the acute phase are dependent upon antioxidant action and also upon protection of healthy tissue by the tumor necrosis factor. Stimulation of synthesis of this factor within the body is caused by multiple toxins. Hence, the therapeutic effect occurs rapidly (twenty to thirty minutes after administration), and one or two injections within a one-day period are sufficient for complete elimination of pathological indications.

The effect of the drug's mode of action has been demonstrated experimentally in relation to a model for endotoxic shock. Administration of the drug five minutes after endotoxin inoculation (until clinical symptoms of shock appeared) wholly prevented development of intoxication symptoms and diarrhea. Moreover, administration of the drug subsequent to clinical appearance of intoxication symptoms and diarrhea provided alleviation of diarrhea and of intoxication symptoms.

The sodium salt of 5-aminophthaloylhydrazide was shown to be effective for proctitis attributable to radiation therapy, whereas current methods of treating this disorder require use of combinations of drugs and are of limited effectiveness.

5-aminophthaloylhydrazide also provided favorable results in treating disorders of the liver, including conditions of toxic origin (carbon tetrachloride poisoning) and postviral infections. Experimental administration of doses of 10 to 20 mg/kg to animals produced a significant decline in the mortality rate among mice exposed to carbon tetrachloride. Whereas the mortality rate attained a 65 percent level in the control group after the latter toxic substance was administered, it declined to 14 percent in the test group. In testing of the drug upon volunteer patients, who received doses of 2 to 5 mg/kg per day (initial phase of chronic stage after viral hepatitis B), symptoms were eliminated and previously impaired hepatic functions were restored.

Even the extremely uncomfortable symptoms occurring during intensification of chronic hemorrhoids (pain, hemorrhaging, etc.) diminish rapidly. In specific terms, the pain syndrome can be alleviated thirty minutes after rectal administration of the drug. Similarly, anal fissures have represented a difficult problem for modern medicine to resolve. In this instance, the inflammatory component is associated with a morphological defect. With rectal administration of the drug, significant alleviation of the pain syndrome was obtained after twenty to forty minutes, and other symptoms were also eliminated by the end of the first day of treatment.

Recurrences were not observed after five to six days of treatment, and regeneration of the mucosae was visually observable.

Gastrointestinal diseases in large livestock species represent a distinct problem. In order to alleviate dyspepsia in piglets and calves, antibiotics which promote development of bacteriolysis and changes in the immune system are widely used at the present time.

Use of an environmentally safe and effective mixture of 5-aminophthaloylhydrazide and its sodium salt in a 1:1 proportion produces elimination of intoxication symptoms two to three hours after intramuscular administration. In 80 percent of the cases involving piglets and in 60 percent of the cases involving calves, it was unnecessary to proceed with further administration of the drug. Administration occurring twenty-four to forty-eight hours after initial administration caused diarrhea to cease. Bacteriological analysis taking place on the fourth or fifth day after the start of treatment provided negative results in 85 percent of the cases. Selection of dosage levels for this particular drug is of fundamental importance. Indeed, dosage depends directly upon the form and duration of the disease, as has been demonstrated. During the initial phases of development of a pathological process, doses of the drug should vary between 10 and 25 mg/kg, but, in more advanced phases, doses are to be increased to 40 to 50 mg/kg. Dyspepsia in piglets which are ten to twenty days old can only be eliminated by administering massive quantities of drugs (5-aminophthaloylhydrazide and its sodium salt) which have been combined in a 1:1 proportion. Moreover, in 60 percent of cases, repeated administration with intervals of six to twelve hours is required.

Mastitis, which is the most frequent disease among adult cattle (cows), can also be treated with 5-aminophthaloylhydrazide. Nevertheless, in order to eliminate pathological symptoms, combined use of the drug with 10 percent to 30 percent DMSO applications is required, with intramuscular administration of the drug continuing for two to five days.

It is possible to obtain favorable results by using 5-aminophthaloylhydrazide to treat skin diseases whose occurrence is accompanied by inflammation. In situations involving external use, in the form of water-soluble applications and ointments, the sodium salt of 5-aminophthaloylhydrazide was more effective. In most instances, application of the drug in a 1 to 2 percent solution for two or three days was sufficient to eliminate symptoms of various diseases. In severe cases (intractable dermatitis, erysipelas, etc.), it was necessary to intensify the effect of the drug by parenteral administration of an adequate dose of 5-aminophthaloylhydrazide (intramuscular or rectal administration) or by using the drug with DMSO as a solvent. In doses of 2 to 5 mg/kg according to weight, the drug did not substantially influence the development of psoriasis. 5-aminophthaloylhydrazide was used in the form of a gargling solution for eliminating inflammation of the mucosae, especially during intensification of chronic tonsillitis, and favorable results were obtained. A more intensive therapeutic effect was observed when the drug was used in a combined form, in a proportion of 1:0.5 to 1:0.1.

Treating autoimmune diseases has presented significant difficulties in medicine. This category of diseases includes glomerulonephritis, non-specific ulcerative colitis, polyarthritis, diffuse sclerosis, etc. The most effective means of treating these diseases currently consist of steroid hormones and immunosuppressive agents.

Use of 5-aminophthaloylhydrazide in the form of rectally administered suppositories and intravenous or intramuscular injections allows alleviation of the principal symptoms of these diseases. Nevertheless, repeated administration of the drug is required in order to accomplish this objective. After an initial phase of treatment, it was possible to prevent subsequent development of pathological processes among 90 percent of the patients and to eliminate pathological symptoms which were not associated with a morphological defect.

Many drugs have been recommended for treating tumors, but the vast majority of these drugs do not truly satisfy the requirements of modern medicine, inasmuch as they only allow insignificant retardation of the growth of tumors.

The biological products which are employed are relatively effective, although a series of complications and side effects may arise. Hence, their use is considerably restricted by this aspect. The tumor necrosis factor (TNF), which is a natural metabolite whose effects upon tumor tissue can enhance use of the drug in question belongs to this particular category of products.

The method of administering the drug in increasing doses, with an increased frequency of administration, where an interval of forty-eight to seventy-two hours is adopted initially, with subsequent daily administration, ensures inhibition of the expansion of malignant tumors. If the drug is combined with radiation therapy (total dose of 60 to 90 g), the effect upon its action is intensified.

Among three patients to whom the drug was administered, favorable results represented by reduction of the dimensions of tumors and by an improvement in their general condition were observed.

In treating AIDS, which is currently incurable, daily administration of 5-aminophthaloylhydrazide in doses of 5 to 15 mg/kg according to weight is required for an extended period.

It was therefore possible to achieve significant prevention or reduction of complications associated with this serious disease, and, as a result, to extend patients' life-spans considerably. Standard doses used for treating inflammatory diseases were found to be of limited effectiveness in these situations.

EXAMPLE 1

Experiments with piglets

Experiments were performed with piglets weighing from 30 to 40 kgs, which were affected by dysentery.

During the first series of experiments, the sodium salt of 5-aminophthaloylhydrazide was administered to nine piglets in a dose of 50 mg/kg. The animals' condition improved within sixty minutes after administration of the drug, and diarrhea ceased. Nevertheless, symptoms reappeared six to seven hours later in one group of animals. This factor rendered repeated administration of the drug necessary.

In the second series of experiments, involving sixteen animals with the same pathological condition, 5-aminophthaloylhydrazide was administered in doses of 20 and 50 mg/kg of body weight. Among this group, the therapeutic effects of 5-aminophthaloylhydrazide were only observed in six instances, and symptoms of dysentery reappeared at the end of the first day.

In the third series of experiments (twelve animals), 4-aminophthaloylhydrazide and 5-aminophthaloylhydrazide were used in doses of 10, 25, and 50 mg/kg in order to treat diarrhea. The therapeutic effect of the drug was relatively insignificant, however.

In the fourth series of experiments, 5-aminophthaloylhydrazide was administered to eight animals in doses of 50 mg/kg. The drug was of limited effectiveness in alleviating diarrhea, although its effects were observable at the end of the first day after administration began.

In the fifth series, a combined product consisting of the sodium salt of 5-aminophthaloylhydrazide mixed with 5-aminophthaloylhydrazide in 1:1 and 1:0.5 proportions was administered to eleven animals.

For 80 percent of the cases, a single administration of this compound was sufficient to relieve diarrhea and the accompanying symptoms two or three hours after administration. Changing the proportion of derivatives to 1:0.3 or 1:0.1 was not accompanied by therapeutic effects. Nevertheless, greater therapeutic effectiveness in treating animals affected by an acute intestinal infection was obtained when 5-aminophthaloylhydrazide and its sodium salt were combined in a 1:1 proportion. On account of technical difficulties, use of other combinations, such as a 1:2 proportion or a 2:1 proportion, was not considered.

EXAMPLE 2

Treatment of proctosigmoiditis

Treatment was provided for nine patients affected by proctosigmoiditis; their ages were between forty and fifty-five years. These patients had complained of irregular defecation, protrusion of the mucosae from the anus, and minor pain in the ileum, on the left side.

During visual examination of the intestine, it was observed that the mucosae of the rectal and sigmoid portions of the colon were affected by edema. In addition, images of the capillary network were blurred, and a fibrous film was present within limited segments. The drug was administered to these patients in the form of rectal suppositories, in doses of 100 mg per day, subsequent to enemas. After initial administration of the drug, the previously cited symptoms and pain disappeared within one day, and the patients' sleep was undisturbed. By the seventh day, the patients no longer complained of symptoms. In RRS (rectosigmoidoscopy) procedures performed during checkups, renewal of normal conditions was observed within the rectal mucosae and within the sigmoid colon.

EXAMPLE 3

Treatment of acute hemorrhoids

The drug was used in the form of suppositories in 0.1 g doses once daily, in order to treat acute hemorrhoids in patients whose ages were from twenty to sixty years. Seventeen to thirty minutes after insertion of the suppository into the anus, pain within the anal area ceased, and these patients were able to sleep undisturbed. Twelve hours later, significant shrinkage of the inflammatory process and reduction of edema in hemorrhoidal nodes was observed, while defecation ceased to be painful. By the fifth day, the inflammatory process and enlargement of hemorrhoidal nodes had entirely disappeared. The patients recovered fully. In contrast, treating acute hemorrhoids with previously known methods has required twenty-one days.

EXAMPLE 3A

N., a male patient who was thirty-seven years of age, had been admitted to a clinic because he had complained of lethargy and continuous non-acute pain in the right hypochondrium. His medical background indicated that he was affected by hepatitis B of the viral type, which he had contracted eight months earlier. Objective analysis revealed scleral jaundice, and palpation of the abdomen was painful in the vicinity of the right hypochondrium. His liver had enlarged by 1.5 to 2 centimeters.

The reaction for bile pigments within urine was positive. Total bilirubin had increased one and one-half times, while ASt and ALt were two times the normal levels. Extensive alteration of the liver was observed during an ultrasound examination.

Rectal suppositories containing the drug, which was to be administered in doses of 100 mg per day for ten days, were prescribed for this patient. On the third day, the patient's condition improved, and his lethargy, as well as pain in the right hypochondrial area, disappeared. On the tenth day, biochemical blood data attained normal levels. The bile pigments reaction was negative. No pathological conditions affecting the liver were observed during an ultrasound examination.

Observation of the patient during the six subsequent months demonstrated an absence of chronic development of the process.

EXAMPLE 4

Treatment of chronic anal fissures with pain syndrome

Treatment was provided for eleven patients who had been affected by the previously cited condition for more than two years and whose ages varied from twenty-seven to sixty years. Methods which had been employed prior to this point had failed to be effective. Examination was not possible on account of acute pain in the anus and intense spasms affecting the anal sphincter.

The drug was administered to this group of patients in the form of suppositories, in doses of 100 mg every twelve hours, during a five-day period. Pain ceased twenty to thirty minutes after initial administration of the suppositories, and the patients were able to sleep undisturbed. After administration of the third suppository, defecation became painless, and spasms affecting the sphincter diminished. By the fifth day, the patients had practically recovered. Digital examination of the rectum was painless.

EXAMPLE 5

Treatment of chronic inflammatory process affecting the female genitalia

Treatment was provided for eleven women between twenty-three and forty-three years of age. They had been affected by chronic inflammation for more than five years, and various treatment methods had been unsuccessful.

The drug was administered to these patients in the form of rectal suppositories (to be inserted at night), in doses of 100 mg once each day, for a five-day period. Subsequently, vaginal insertion was performed for an additional period of two days. On the second day after the commencement of treatment, the therapeutic effect was observable. There was a significant decrease in vaginal secretions, which ceased completely by the fifth day, with healing occurring by the eighth day.

Clinical observations were confirmed by laboratory analysis of vaginal secretions in each instance.

EXAMPLE 6

V., a female patient who was forty-seven years of age, was observed to be affected by suppuration of a paracolostomy incision in the left inguinal region, with inflammatory infiltration of adjacent soft tissues, subsequent to abdominoperineal excision of the rectum on account of an adenocarcinoma. The patient cited pain in the region affected by infiltration, and an increase in body temperature was observed. A suppository containing 200 mg of the drug was applied to the incision. Pain ceased twenty to thirty minutes after administration of the drug. Six hours later, her temperature declined. An identical dose of the drug was administered again twelve hours later. Edema within soft tissues had decreased significantly twenty-one hours after the commencement of treatment. Treatment was continued for six days, and, at the end of this period, the wound was wholly devoid of pus. It is therefore possible to conclude that it is possible to use the drug in the previously indicated doses for eliminating inflammatory processes during the post-operative period.

EXAMPLE 7

Treating Malignant Tumors

Kh., a patient who was thirty years of age, had been diagnosed with an anal adenocarcinoma seven months earlier.

The diagnosis had been verified histologically. The patient cited pain in the anus, constipation, difficulty in defecating, and secretion of mucus and blood from the anus. On account of the patient's categorical refusal to undergo surgery for abdominoperineal excision of the rectum, radiation therapy had been provided in doses of 45 g. During a subsequent examination, fifty days after radiation therapy had begun, no development of the anal tumor was observed. Forty days later, the patient underwent another cycle of radiation therapy, with doses of 45 g. During the next thirty days, the drug was administered in doses of 100 mg every four hours, in the form of rectal suppositories. During the next examination, reduction of the tumor was observed. For the next thirty days, the dosage of the drug was increased, and intramuscular administration of 100 mg per day was provided for this patient, along with a rectal suppository (100 mg).

During the next examination, it was determined that the anal tumor had been reduced by two-thirds in relation to its initial dimensions. It had acquired a dense and elastic consistency, and limited mobility was observed. In addition, it was covered with a normal mucous membrane.

Subsequently, an improvement of the patient's general condition was observed.

By treating a malignant tumor with a combination of radiation therapy and administration of the drug, reduction of the tumor's dimensions was therefore obtained within a brief period and symptoms of intoxication were eliminated.

EXAMPLE 8

R., a female patient who was forty-seven years of age, was affected by a perineal cutaneous melanoma accompanied by lesions within the anal wall and tumors within lymph nodes in the left inguinal region.

This diagnosis had been confirmed histologically.

Localized excision of the tumor was performed, and the group of lymph nodes in the left inguinal region was removed.

When the patient was examined during a checkup forty days thereafter, hardening was observed in the vicinity of the postoperative scar. This phenomenon was indicative of the onset of recurrence of the tumor. Intramuscular administration of the drug in 100 mg doses was provided on alternating days. On the third day after the commencement of treatment, abnormal salivation began, and vomiting occurred on the fourth day, along with an increase in diuresis. These symptoms gradually ceased on the thirteenth and fourteenth days. By increasing the dosage of the drug, it was possible to increase its therapeutic effect.

Beginning on the twentieth day, the drug was administered in 100 mg intramuscular doses every day. During a checkup thirty days later, disappearance of infiltration in the region of the postoperative scar was observed. This phenomenon demonstrated dissolution of tumoral tissue, and it was likewise confirmed by a subsequent histological examination.

EXAMPLE 9

Endotoxin experiments

These experiments were performed upon rabbits. *Salmonella typhinurium* endotoxin which had been purified by Bolvin's method was used in doses of 1 mg/kg according to body weight. In the first series of experiments, endotoxin inoculation resulted in the onset of intoxication symptoms only ten minutes after the experiment began, with more significant clinical manifestations occurring one hour thereafter.

During the second series of experiments, the drug was administered intravenously in doses of 15 mg/kg according to body weight when clinical manifestations appeared (thirty to forty minutes after the commencement of the experiment). Reduction of intoxication symptoms was observed five to ten minutes after administration of the drug, and diarrhea ceased completely. During the third series of experiments, the drug was administered five minutes after endotoxin inoculation. In this instance, partial alleviation of symptoms was observed.

During the ensuing series of experiments, 25 mg/kg of the drug, according to body weight, was administered to the animals, and complete alleviation of intoxication symptoms and diarrhea was obtained.

Conclusion: according to the duration of the respective disease, 15 to 25 mg/kg doses of 5-aminophthaloylhydrazide prevent or eliminate intoxication symptoms.

EXAMPLE 10

Induced abortion

Experiments were performed upon twenty pregnant rabbits. During the first series of experiments, abortions were observed in eighty percent of the animals, at the peak of clinical manifestations of intoxication, forty to sixty minutes after inoculation with *Salmonella typhinurium* endotoxin, in a dose of 1 mg/kg according to body weight.

During the second series of experiments, the drug was administered in doses of 15 mg/kg, and abortion was prevented in seven among every ten rabbits, notwithstanding the endotoxin.

It was therefore demonstrated that the drug was capable of preventing premature abortion resulting from intoxication in the animals which were used in this experiment.

EXAMPLE 11

It is known that diarrhea often occurs in newborn calves, at the point when artificial feeding is introduced. In order to prevent or alleviate its occurrence, the drug was used in a combined form, and it was particularly effective.

Experiments were performed upon twenty newborn calves.

20 mg/kg intramuscular doses of a combined drug consisting of 5-aminophthaloylhydrazide and its sodium salt in a 1:1 proportion were administered on the first day after birth. Two days later, the drug was administered again in doses of 10 mg/kg according to body weight.

A positive therapeutic effect was obtained, with diarrhea being eliminated in 80 percent of the cases.

It was therefore concluded that it is possible for the combined drug to be used to prevent diarrhea from occurring in newborn calves.

EXAMPLE 12

Suppuration and abscesses affecting the jaw necessarily require surgical intervention. Operations are only possible, however, after elimination of the inflammatory reaction occurring in adjacent tissue. Characteristic clinical symptoms of inflammation such as pain, edema, uncomfortable sensations, fever, etc. were observed in all of the eighteen patients being studied.

The patients were subdivided into three groups according to alphabetical order. The drug was prescribed for every patient on one occasion, although different dosages were adopted (1 mg/kg; 2 mg/kg; 4 mg/kg). Another examination of the patients, one day after administration of the drug, offered the following conclusions: no therapeutic effect had occurred within the first group; a therapeutic effect had occurred among four patients in the second group; and a therapeutic effect was observed in each of the six patients constituting the third group.

Histological analyses which were performed for a sample consisting of five patients from the different groups confirmed the results which had been obtained.

Conclusion: minimum therapeutic doses of the drug— from 2 to 4 mg/kg, according to the patient's body weight.

EXAMPLE 13

The antitoxic effect of the drug was confirmed among patients with acute intestinal infections.

Example: N., a male patient who was forty-two years of age, was admitted to a hospital clinic on account of spasmodic pain in various portions of the abdominal region, nausea, vomiting, recurrent fluid stools which did not contain extraneous substances (blood, mucus), a higher body temperature, headaches, and lethargy. 200 mg of the drug in an isotonic aqueous solution was administered to this patient. Forty to fifty minutes later, his condition improved, and a significant decrease in abdominal pain occurred, along with cessation of diarrhea.

One day after admission to the clinic, all of the symptoms of intoxication had disappeared. The patient was released in satisfactory condition on the third day.

Fecal cultures for bacillary dysentery and Salmonella were negative.

EXAMPLE 14

Treatment of non-specific ulcerative colitis and Crohn's disease

Treatment was provided for three patients whose ages were between thirty-three and forty-one years and who were affected by non-specific ulcerative colitis in the intense form of its active phase, and for a patient who was forty-two years of age and was affected by Crohn's disease within the colon.

These patients complained of periodic worsening of their symptoms over periods of three to five years.

Notwithstanding continuous treatment, including hormonal therapy, the patients' condition became worse. They lost weight, they cited constant pain within the large intestine, frequent voiding of fluid stools containing mucus, blood, and pus, as often as fifteen times daily, pains in their joints, and skin eruptions. Considerable quantities of pus were observed within the rectum during rectosigmoidoscopy, and the mucosae were usually edematous, enlarged, porous, and filled with blood.

100 mg per day of the drug was administered intravenously to these patients for three days. Thirty minutes after intravenous administration, abdominal pain and pain in their joints lessened, and the patients' condition already improved on the first day. During the first three days, frequency of defecation was reduced. Because no positive trend was observed subsequently, the dosage of the drug was doubled, and the frequency of intramuscular administration was modified (every twelve hours).

On the sixth day, the patients cited decisive improvement. They were no longer experiencing pain, their skin eruptions had disappeared, and defecation was occurring two or three times daily, without the continued presence of blood or pus.

On subsequent days, intramuscular administration of the drug was provided once daily, along with a 100 mg rectal suppository.

On the fourteenth day, the patients did not cite further difficulties, and defecation had nearly become normal, occurring once or twice each day.

Rectosigmoidoscopy examinations did not reveal the presence of pus or blood, although traces of an inflammatory process were observed within mucous membranes.

EXAMPLE 15

V., a female patient who was thirty-seven years of age, had undergone a mastectomy on account of cancer affecting the left breast. During subsequent years, she had undergone radiation therapy and chemotherapy on multiple occasions on account of metastatic tumors.

At the point when treatment began, the patient's condition was already severe on account of cancerous intoxication.

She had lost her appetite and was experiencing persistent intense pain within the left humeral cingulum and within the upper left arm.

Advanced lymphatic stasis was observed above the previously cited regions and in the left subaxillary region. On account of the severity of the patient's condition, intramuscular administration of the drug in 100 mg doses every two days was initiated. After the first injection of the drug, the intensity of her pain decreased significantly. On the fourth day after the commencement of treatment, abnormal salivation began.

On the sixth day, vomiting began, and the patient's stools were malodorous. On the seventh and eighth days, her urine became more dense, frequent urination began, and her perspiration acquired a rather foul odor. On the thirteenth and fourteenth days, edema within the left humeral cingulum, the left arm, and the left subaxillary region had diminished significantly.

On the twentieth day, the patient's condition improved, and her appetite was restored. After the twentieth day, intramuscular administration of the drug took place on alternate days. Subsequently, a steady improvement in the patient's general condition was observed.

EXAMPLE 16

Treatment of proctitis and cystitis occurring after radiation therapy

B., a male patient who was thirty-five years of age, complained of burning sensations in the anus, along with frequent and painful urination, after having received radiation therapy for a period of forty-five days. During a rectosigmoidoscopy examination, intense edema and contact hemorrhaging within the rectal mucosae were observed above the tumor. The diagnosis was: proctitis and cystitis arising from radiation therapy. On account of a lack of specific therapeutic measures, the drug was prescribed for the patient according to a dose of 100 mg per day. Observation of the patient for three days demonstrated the absence of any significant clinical effect, and the dosage of the drug was therefore increased.

Rectal suppositories containing 100 mg of the drug were administered to the patient for ten days, in the morning and in the evening. Anal burning and painful urination diminished in one day. The patient began to sleep adequately. By the third day, pain and burning were no longer present. Urination became normal on the fifth day, after the dosage was increased. Ten days later, during a rectosigmoidoscopy examination, regeneration of the capillary network within the rectal mucosae was observed.

EXAMPLE 17

N., a male patient who was forty-two years old, had been admitted to a clinical department with the following diagnosis: erysipelas on the left foot. During the patient's hospitalization, his condition was determined to be of moderate severity. An edematous portion of skin protruding from the cutaneous surface was observed in the front portion of his left foot. This area was painful and warm when it was palpated. General loss of strength and a higher body temperature, up to 38.6° C., were also observed.

The respective compound was applied to the affected area of the patient's skin in the form of a 1 percent ointment. Suppositories containing 100 mg of the drug were prescribed at the same time. Pain became less intense five to six hours after administration, and, within twenty-four hours, congestion and edema within the patient's foot had diminished.

His general condition improved thereafter.

Subsequently, the patient was treated with the drug in the form of suppositories for five days.

By the end of the sixth day, the patient no longer cited difficulties, and a pigmented segment of skin remained in the affected area.

On the seventh day after the commencement of treatment, the patient was released in presumably satisfactory condition.

EXAMPLE 18

Treatment of dermatitis of unknown etiology

A patient who was seven months old had experienced dermatitis of unknown etiology since the age of two weeks. Skin on the child's face, within the humeral cingulum, and on the legs had been affected.

Throughout this period, various methods had been applied without success.

The patient was treated for fourteen days.

The affected cutaneous areas were treated three times daily with a water-soluble emulsion containing 30 mg of the drug, and, on alternating days, suppositories containing 50 mg of the drug (5 mg/kg according to weight) were administered rectally.

After the second day, the affected cutaneous areas began to become drier, and epithelization was completed by the fourteenth day.

EXAMPLE 19

N., a thirty-nine year old male patient, was admitted to a clinical department with the following diagnosis: erysipelas of the right leg. Objective indications included: a congested segment of skin on the front surface of the leg; this area protruded from the surface and it was painful when palpated. Body temperature: 37.8° C. The patient was experiencing generally disagreeable sensations, and intense pain in the vicinity of the inflamed area.

A 4 percent solution of the drug within a 20 percent DMSO solution was applied to the affected cutaneous area. Pain diminished forty to sixty minutes after the commencement of treatment.

Congestion diminished twenty-four hours later. The patient did not cite pain, and his general condition improved. Treatment was continued for three days, until complete elimination of pathological symptoms.

It is therefore possible to affirm that the solution containing 4 percent of the drug combined with 20 percent DMSO possesses significant therapeutic effectiveness in terms of reducing clinical manifestations of the disease.

EXAMPLE 20

I., a thirty-seven year old male patient who was hospitalized, cited frequent fluid stools which contained mucus and blood, occurring as many as seven times daily. The well-known symptoms of intoxication were observed. During a rectosigmoidoscopy examination, pronounced indications of inflammation were observed within the rectum.

The preliminary diagnosis which was suggested was: non-specific ulcerative colitis.

Treatment began with intramuscular administration of 100 mg doses of the drug, once daily.

Because no therapeutic effects had been observed three days later, the daily dose was doubled. Even in that instance, the therapeutic action of the drug was still not observable.

On the fifth day, AIDS was diagnosed on the basis of laboratory analyses.

The daily dosage of the drug was then increased to 400 mg. On the third day after the patient's dosage had been increased, diarrhea disappeared, symptoms of intoxication disappeared, and his general condition improved.

When daily administration of the drug was continued, further symptoms of the disease did not appear.

It is therefore obvious that it is possible for the drug to be used with favorable results in combatting the complications which arise in patients affected by AIDS.

We claim:

1. A method for treating disorders selected from the group consisting of ulcerative colitis, Crohn's disease, diffuse sclerosis, diarrhea, proctitis, hemorrhoids, anal fissures, dyspepsia, intestinal infection and proctosigmoiditis, in mammals comprising the steps of:

initially parenterally administering a dosage of a drug being 5-aminophthaloylhydrazide or a pharmaceutically acceptable salt of the drug or a mixture of the drug and the salt, at a dosage of 5 to 50 mg/kg according to kg of body weight, and at an initial low frequency of administration; and thereafter parenterally administering the drug, salt or mixture of the drug and salt, at the dosage and at a higher frequency of administration.

2. The method according to claim 1, including administering a sodium salt of 5-aminophthaloylhydrazide as the pharmaceutically acceptable salt.

3. The method according to claim 2, including administering a mixture of 5-aminophthaloylhydrazide and a sodium salt thereof, in proportions ranging from 1:1 to 1:0.5.

4. The method according to claim 3 including, administering the mixture intravenously.

5. The method according to claim 3 including, administering the mixture intramuscularly.

6. The method according to claim 1 including, administering 5-aminophthaloylhydrazide intravenously.

7. The method according to claim 1 including, administering 5-aminophthaloylhydrazide intramuscularly.

8. A method according to claim 1 including, administering the 5-aminophthaloylhydrazide or salt thereof in a solution buffered to pH 7.8 to 8.0, the solution being administered parenterally.

9. A method according to claim 1, wherein the initial low frequency of administration is about every one to three days, and the higher frequency of administration is about once or twice daily.

10. A method according to claim 8, wherein the initial low frequency of administration is about every one to three days, and the higher frequency of administration is about once or twice daily.

* * * * *